(12) United States Patent
Price et al.

(10) Patent No.: US 6,344,047 B1
(45) Date of Patent: Feb. 5, 2002

(54) INSTRUMENT FOR INSERTING A PUNCTUM PLUG AND METHOD FOR MANUFACTURING THE INSTRUMENT

(75) Inventors: Bret Price, San Antonio, TX (US); Nicholas J. Webb, Wrightwood, CA (US)

(73) Assignee: Eagle Vision, Memphis, TN (US)

( * ) Notice: Subject to any disclaimer, the term of this patent is extended or adjusted under 35 U.S.C. 154(b) by 0 days.

(21) Appl. No.: 09/495,953

(22) Filed: Feb. 2, 2000

(51) Int. Cl.7 .................................................. A61F 17/00
(52) U.S. Cl. ........................................ 606/191; 604/298
(58) Field of Search .................................. 606/191, 104, 606/109, 140, 141, 170, 205, 174, 1; 128/831, 887, 846, 848; 604/298, 294, 8, 9

(56) References Cited

U.S. PATENT DOCUMENTS

| | | |
|---|---|---|
| 3,949,750 A | 4/1976 | Freeman |
| D295,445 S | 4/1988 | Freeman |
| 5,053,030 A * | 10/1991 | Herrick et al. ............... 604/198 |
| 5,283,063 A | 2/1994 | Freeman |
| 5,355,871 A | 10/1994 | Hurley et al. |
| 5,417,651 A | 5/1995 | Guena et al. |
| 5,423,777 A | 6/1995 | Tajiri et al. |
| 5,437,625 A | 8/1995 | Kurihashi |
| 5,634,918 A | 6/1997 | Richards |
| 5,741,292 A | 4/1998 | Mendius |
| 5,830,171 A | 11/1998 | Wallace |
| 6,149,684 A * | 11/2000 | Herrick ........................... 604/8 |

OTHER PUBLICATIONS

"Why do my Eyes Feel This way?", 1988 RCT Ophthalmics, Inc., FCI.
"What Causes Dry Eye?", FCI.
"Punctum Plug", Bulletin PP 9/99, Surgidev Corporation.
"Soft Plug", Donawa Italia Srl, Oasis.
"The Parasol", Odyssey Medical, Inc.

\* cited by examiner

Primary Examiner—Kevin Truong
(74) Attorney, Agent, or Firm—Marc S. Kaufman; Nixon Peabody LLP

(57) ABSTRACT

An instrument for inserting a lacrimal punctum plug and a method of manufacturing the instrument. A body having an insertion portion, a flexible portion, and a handle portion is molded around a shaft. Deforming the flexible portion reduces the effective length of the shaft to draw the shaft into the instrument. A plug supported on the shaft is released when the shaft is withdrawn. Finger pads on the flexible portion properly position fingers of medical personnel using the instrument.

20 Claims, 7 Drawing Sheets

INSTRUMENT FOR INSERTING A PUNCTUM PLUG AND METHOD FOR MANUFACTURING THE INSTRUMENT

BACKGROUND OF THE INVENTION

1. Field of the Invention:

The invention relates generally to the treatment of ocular surface disease. More specifically, the invention relates to an instrument for inserting a plug in a lacrimal punctum for treatment of ocular surface disease such as Dry Eye Syndrome.

2. Description of the Related Art:

The surface of the eye and the inner surface of the eyelid are moisturized by tears constantly produced by tear glands around the eye. A tiny hole, known as the "lacrimal punctum", at the inner corner of each upper and lower eye lid margin drains the tears away through a duct known as the "lacrimal duct" to maintain the proper moisture level balance of a "tear film" on the surface of the eye. The tear film serves to bath and lubricate the eye through a delicate balance of an outer lipid (oily) layer, a middle aqueous (watery) layer, and an inner mucin (mucus) layer. As shown in FIG. 1 the lacrimal duct consists of the upper punctum 10, lower punctum 12, upper canaliculus 14, lower canaliculus 16, common canaliculus 18, lacrimal sac 20 and nasolacrimal duct 22. Nasolacrimal duct 22 opens into the interior nasal meatus in the nasal cavity behind nose M (shown as a dotted line).

A collection of symptoms called "keratoconjunctivitis sicca" or "keratitis sicca", commonly known as "Dry Eye Syndrome", occur when the proper moisture level is not obtained on the eye surface due to an imbalance between the quantity or quality of tears secreted by tear glands, and the quantity of tears drained through the lacrimal duct or lost through evaporation. Dry Eye Syndrome results in dry spots on the eye that cause a feeling of a dry sensation of the eyes or even a feeling of an adhesion sensation, known as "asthenopia", between the eye lid and the surface of the eye. Dry Eye Syndrome can cause general discomfort, particularly when wearing contact lenses. Further, if left untreated, Dry Eye Syndrome can result in damaged tissue and possibly scarring on the cornea leading to irreversible sight threatening conditions.

Dry Eye Syndrome is easily diagnosed through well established diagnostic tests. However, there is no known cure for Dry Eye Syndrome. Several approaches to treatment of Dry Eye Syndrome are known conventionally. For example, it is known to introduce artificial tears into the eye in the form of eye drops or the like. However, artificial tears only provide temporary relief and thus must be applied at regular intervals. Also, prolonged use of artificial tears may suppress natural tear generation and thus can lead to further aggravation of Dry Eye Syndrome. Also, various surgical procedures are known for occlusion of the upper and for lower puncta to reduce or eliminate the amount of tears from draining through the lacrimal duct. Surgical procedures, such as cauterization of the puncta, and are relatively invasive and complex.

Accordingly the less invasive procedure of inserting punctum plugs has become popular. In particular, the punctum is dilated and a plug is inserted therein to occlude the punctum. A typical punctum plug includes a cylindrical or conical body, and a coaxial hole for receiving a tip of an insertion instrument to thereby permit the plug to be supported on the insertion instrument. It can be appreciated that a punctum plug is a very small device that must be precisely inserted into the punctum at the proper depth. Over insertion or under insertion can adversely affect the efficacy of the plug.

A variety of instruments are known for inserting punctum plugs. For example, Lacrimedics, Inc. sells a punctum plug preloaded on the tip of a pin stuck into a piece of foam. The pin is used to push the plug into a punctum. After the plug is properly seated, the pin is withdrawn. However, the pin must be precisely held to position the plug in a neutral position during withdrawal, i.e., it must not be canted to one side, to avoid sticking of the plug to the pin. Such precision is difficult to achieve and thus the pin often sticks to the plug enough to unseat it during withdrawal.

Another known plug insertion instrument is sold under the tradename Michalos Insertion Forceps™ by Eagle Vision, Inc. of Memphis, Tenn. This instrument includes a pin arranged at one tip for supporting a punctum plug, and a gripping hook arranged on the other tip for gripping and securing the plug prior to insertion. After the plug is inserted into a punctum, the gripping hook is released so that the pin can be withdrawn from the plug. However, the pin still may stick to the plug, and the plug can be unseated during withdrawal of the pin.

A punctum plug insertion instrument sold by GWB International, Ltd. includes a trigger mechanism for releasing the plug after insertion. A main cylindrical body has a central wire extending coaxially from one end thereof. A tube is slidably positioned around the central wire. An elliptical spring has one end attached to the main body and another end attached to the slidable tube. A punctum plug is supported on the tip of the wire prior to insertion. When the punctum is properly dilated, the plug is inserted therein and the spring is squeezed to elongate in a longitudinal direction thereby sliding the tube forwardly to move the plug off of the tip of the wire. However, the complex construction of the trigger mechanism, the elliptical spring in particular, makes a poor handle that is awkward to hold and difficult to control. Furthermore, when the trigger mechanism is activated to dislodge the plug, the slideable tube tends to push the plug deeper into the punctum than desired.

U.S. Pat. No. 741,292 discloses a punctum plug insertion instrument having an elongated button as a trigger. One end of the button is fixed to a body of the device and the other end is slideable and fixed to a wire that extends from an insertion tip of the device. Deformation of the button causes the wire to retract into the insertion tip to release a punctum plug supported on an end of the wire. However, the instrument disclosed in U.S. Pat. No. 5,741,292 is relatively complex and difficult to manufacture.

Oasis sells a punctum plug insertion instrument under the tradename Soft plug™ that includes two thin elongated members defining a substantially diamond shaped outboard trigger. A thin metal tube is attached to one end of the trigger and a wire extends through the tube and is anchored at the other end of the trigger. A projection is formed on each elongated member and extends toward the wire. Pressing the elongated members towards one another causes the diamond shaped trigger to increase in length thereby pulling the end of the wire into the tube. Eventually, the projections interact with the wire to bend the wire and decrease the effective length of the wire. The increase in the length of the diamond shaped trigger and the decrease in the effective length of the wire cause the end of the wire to retreat into the tube thus releasing a punctum plug supported on the end of the wire. However, the entire handle of this instrument is effectively a trigger activation mechanism for releasing the plug.

Accordingly, it is difficult to perform the intricate manipulation, including rotation and axial movement, required for insertion of a punctum plug without the prematurely activating the trigger and releasing the punctum plug. Also, it is difficult to activate the trigger without disturbing the inserted plug because trigger activation requires a relatively large stroke. Further the complexity of the device renders it difficult to manufacture. The procedure for inserting a punctum plug requires intricate and delicate manipulation. It is desirable that an insertion instrument have good ergonomics and high tactile sensation and feedback. Further, a small variation in position of the handle of a micro instrument, such as a punctum plug insertion instrument, can result in relatively large insertion errors. Accordingly, the control interface is of critical importance in punctum plug insertion instruments.

SUMMARY OF THE INVENTION

It is an object of the invention to simplify the manufacture of a punctum plug insertion instrument.

It is another object of the invention to improve tactile sensation and feedback during a punctum plug insertion procedure.

It is another object of the invention to improve balance of a punctum plug insertion instrument.

It is another object of the invention to facilitate proper positioning of the operator's fingers on a trigger device of a punctum plug insertion instrument.

It is another object of the invention to facilitate manipulation and release of a punctum plug during an insertion operation.

A first aspect of the invention is an instrument for inserting a plug into a lacrimal punctum comprising an elongated body having a first end, a second end, a handle portion, and a cavity formed in the body to define a flexible portion, and an insertion portion defined on the first end. The plug insertion portion has a passage formed therethrough in communication with the cavity formed in the body. A shaft is coupled to the body and extends through the cavity formed in the body and the passage formed through the insertion portion. The shaft has a support portion defined thereon that is adapted to be received in an aperture formed in a plug. A projection extends from an inner surface of the surface that defines the cavity in the body towards the shaft. Deformation of the flexible portion causes the projection to interact with the shaft to deform the shaft and reduce the effective length of the shaft thereby causing the support portion of the shaft to move from a position in which the support portion of the shaft extends from an end of the insertion portion to a position in which the support portion is substantially contained within the insertion portion.

A second aspect of the invention is a method of forming an instrument for inserting a plug into a lacrimal punctum. The method comprises the steps of forming an elongated body having a first end, a second end, a handle portion, a flexible portion, a cavity defined in the flexible portion, and a plug insertion portion on the first end, forming a passage through the plug insertion portion and in communication with the cavity defined in the body, coupling a shaft to the body, the shaft extending through the cavity defined in the body and the passage formed through the insertion portion and the shaft having a support portion defined thereon that is adapted to be received in an aperture formed in the plug, and forming a projection extending from an inner surface of the body that defines the cavity in the body towards the shaft.

BRIEF DESCRIPTION OF THE DRAWING

The invention is described through preferred embodiments and the attached drawing in which.

DETAILED DESCRIPTION OF THE PREFERRED EMBODIMENTS

Figure 1:
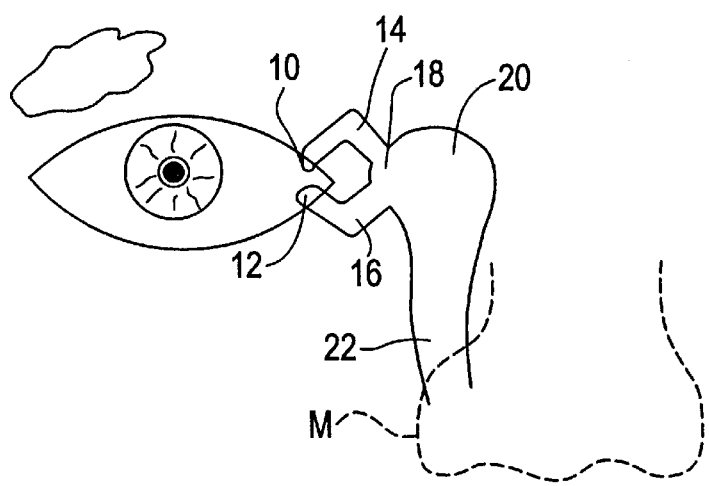
FIG. 1 is a plan view of an eye partially cutaway to illustrates the basic anatomical structure of the lacrimal duct.

FIGS. 2–5 illustrate a first preferred embodiment of the invention. Punctum plug insertion device 30 includes body 40 that is elongated and substantially cylindrical. Body 40 comprises plug insertion portion 42 at a first end thereof, dilation portion 44 at a second end thereof, flexible portion 46 adjacent insertion portion 42 (see FIG. 3), and handle portion 41. As will become apparent below, the entirety of body 40 preferably is made of a somewhat flexible material and flexible section 46 is rendered relatively more flexible than other portions of body 40. For example, body 40 can be molded of a medical grade polycarbonate, medical grade nylon, or any inert, latex-free material that can withstand gamma irradiation for sterilization. Flexible portion 46 defines a trigger portion for releasing a punctum plug as discussed in detail below.

Figure 2:
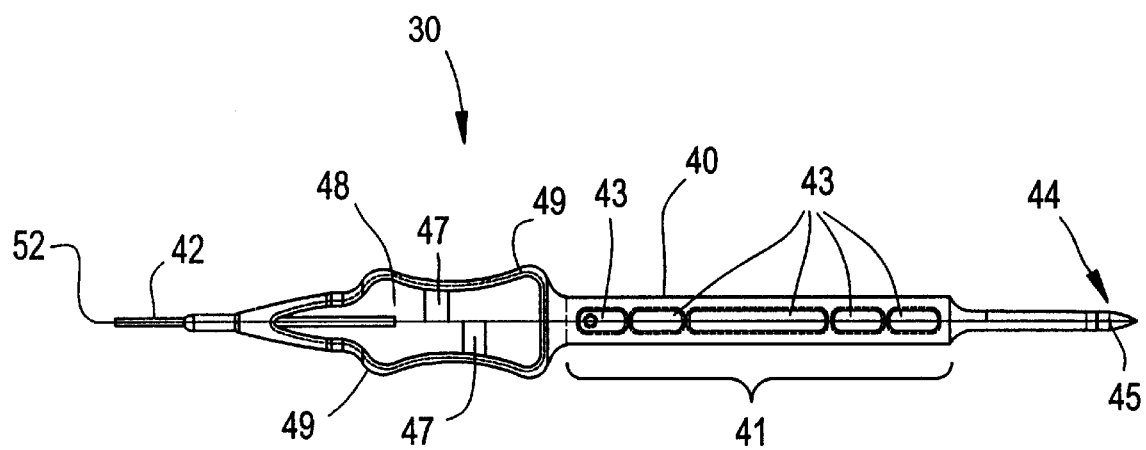
FIG. 2 is a top view a punctum plug insertion instrument in accordance with a first preferred embodiment of the invention.
Figure 3:
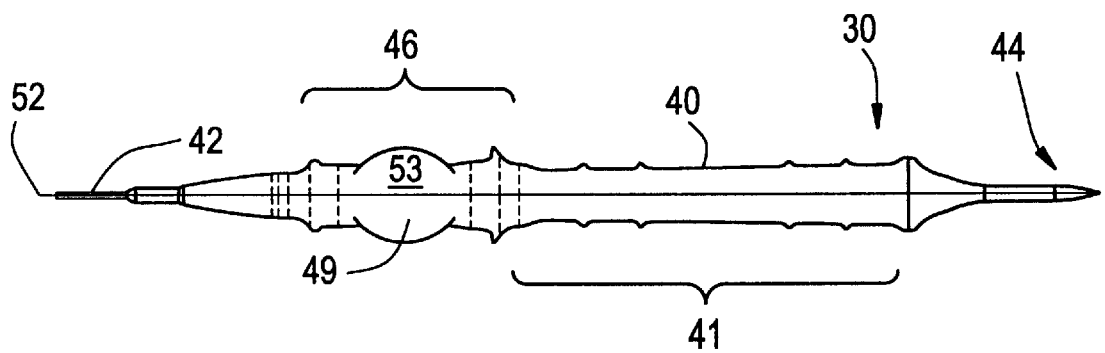
FIG. 3 is a side view of the instrument of FIG. 1.
Figure 4:
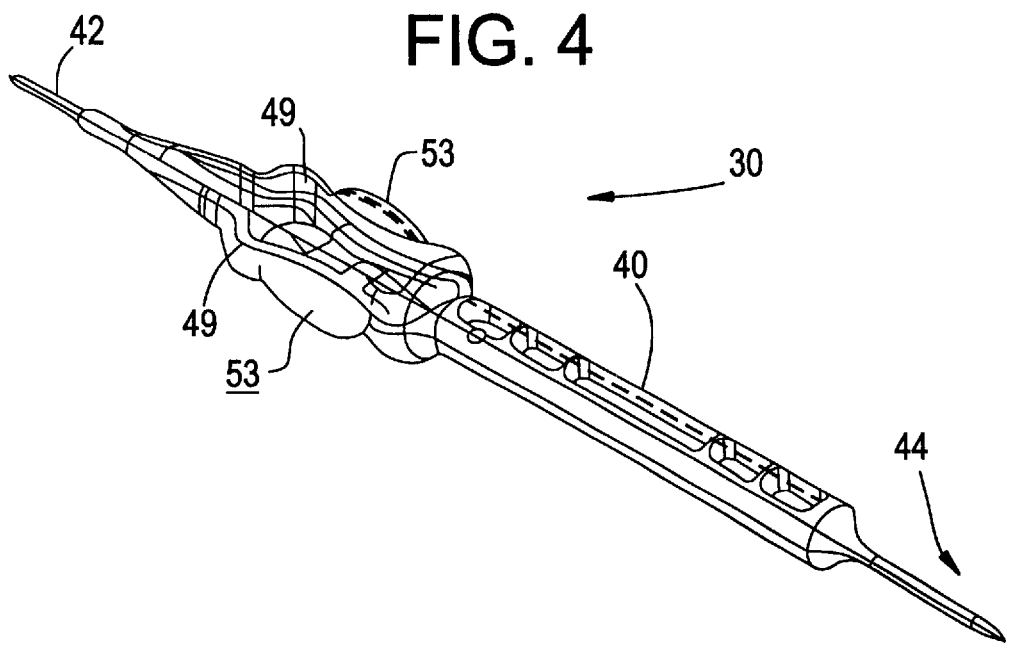
FIG. 4 is a perspective view of the instrument of FIG. 1.
Figure 5:
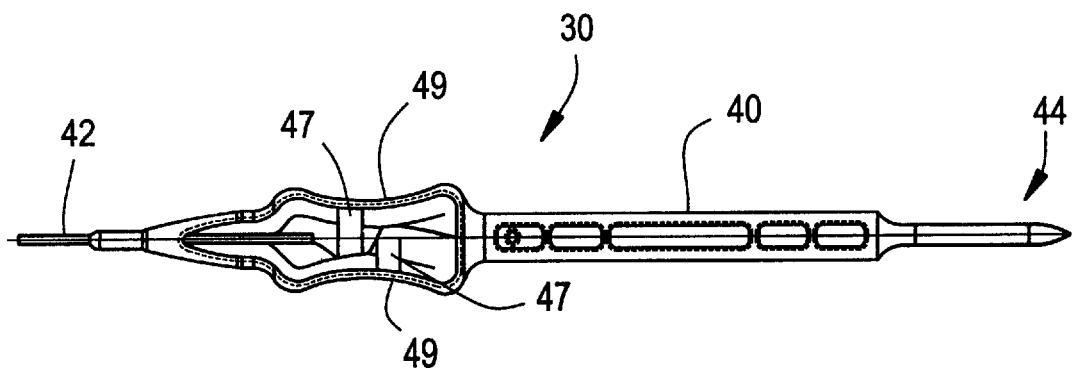
FIG. 5 is a top view of the instrument of FIG. 1 with the trigger portion activated.
Figure 6:
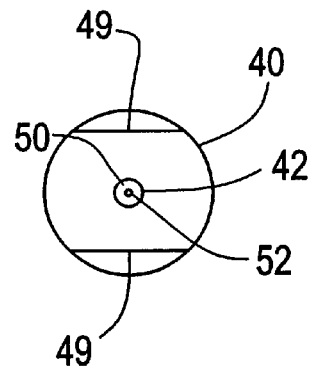
FIG. 6 is an end view of the instrument of FIG. 1

FIG. 2 is a side view of the first preferred embodiment in which it can be seen that cavity 48 is formed in body 40 at a position adjacent plug insertion portion 42. Cavity 48 is defined between branch portions 49 of body 40 that can be relatively thin as compared to handle portion 41 of body 40. Accordingly, branch portions 49 of flexible portion 46 are more flexible than handle portion 41 even though body 40 of the preferred embodiment preferably is molded integrally of a single material as described in detail below. Finger pads 53, as best illustrated in FIGS. 3 and 4, are defined on outer portions of branch portions 49 respectively. Projections 47 are formed respectively on branch portions 49 for reasons discussed in detail below. Shaft 52, a wire in the preferred embodiment, is fixed to handle portion 41 of body 40 and extends through cavity 48, along a surface of projections 47, and through passage 50 formed in plug insertion portion 42 (see FIG. 6). A free end of shaft 52 extends out of plug insertion portion 42 of body 40, in the state illustrated in FIGS. 1–4, to define a plug support portion of shaft 52 on which a punctum plug can be supported as described in detail below. Finger pads 53 preferably are substantially oval in shape and have a concave surface to naturally position the user's forefinger and thumb respectively on instrument 30.

Figure 7:
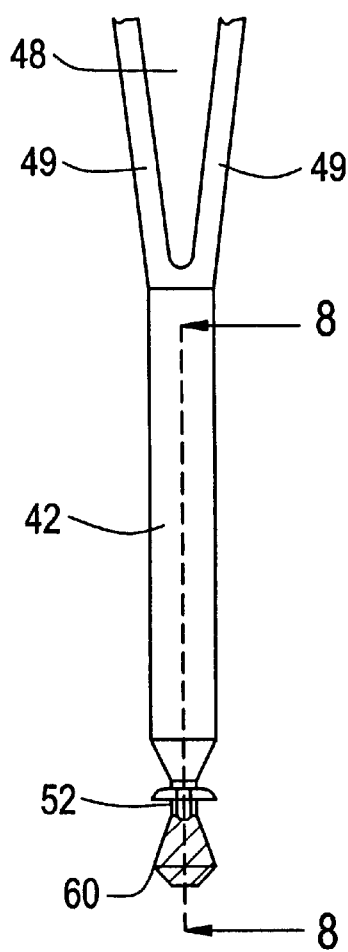
FIG. 7 is a side view of an end of the instrument of FIG. 1 with a punctum plug loaded thereon.

FIG. 7 illustrates the insertion portion 42 of instrument 30 in detail with punctum plug 60 loaded on a support portion of shaft 52. The support portion of shaft 52 extends from insertion portion 42 and is frictionally fitted into a mounting hole of punctum plug 60 to support punctum plug 60 on an end of insertion portion 42. For example punctum plug 60 can be similar to that disclosed in U.S. Pat. No. 3,949,750 issued to Freeman, the disclosure of which is incorporated herein by reference. In this state, i.e. a loaded state, punctum plug 60 is ready to be inserted into a punctum, such as lower punctum 12. However, it is ordinarily desirable to dilate punctum 12 and lubricate punctum plug 60 prior to insertion. Dilation can be accomplished by inserting a tip of dilation portion 44 into the punctum. Preferably, a local anesthetic agent is used to minimize patient discomfort. Dilation portion 44 can be lubricated and then manipulated by grasping handle portion 41 to slowly be inserted into punctum 12 to a desired depth to achieve a desired amount of dilation. Gradations or other markings 45 can be defined on dilation portion 44 to indicate the depth of penetration of dilation portion 44 into punctum 12 and/or the amount of dilation achieved by the penetration depth.

When punctum 12 is properly dilated, punctum plug 60 is lubricated with a suitable medical grade lubricant, such as such as a conventional artificial tear agent, and inserted into punctum 12 by grasping handle portion 41 and gently pushing body 40 linearly and twisting body 40 about a longitudinal axis of instrument 30. Because of the small size of puncta and the delicacy of surrounding tissue, the insertion step must be accomplished accurately and gently. The flexibility of body 40, and the distinction between handle portion 41 and flexible portion 46 (defining a trigger) permits good tactile sensation and feedback to the medical personnel inserting punctum plug 60.

Figure 8:
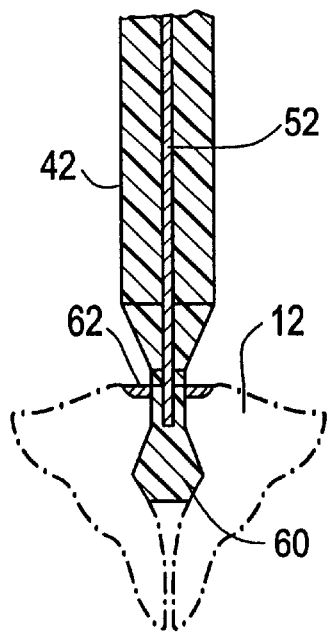
FIG. 8 is a sectional view of an end of the instrument of FIG. 1 taken along line 8—8 of FIG. 7 with a punctum plug inserted in a punctum.
Figure 9:
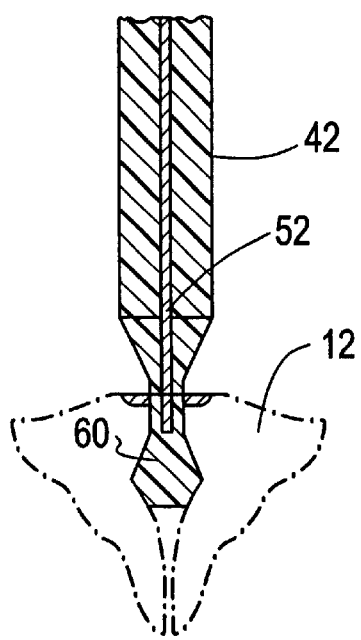
FIG. 9 is a sectional view of the instrument of FIG. 1 taken along line 8—8 of FIG. 7 with the punctum plug released.

As illustrated in FIG. 8, punctum plug 60 preferably is inserted deep enough into punctum 12 so that the top of flange 62 of punctum plug 60 is substantially flush with the rim of punctum 12. As illustrated in FIG. 9, after punctum plug 60 is properly seated in punctum 12, punctum plug 60 is released from insertion portion 42 by simply pressing branch portions 49 towards one another to deform branch portions 49. Deformation of branch portions 49 causes projections 47 to move inward to bend shaft 52, as illustrated in FIG. 2, to thereby reduce the effective length of shaft 52 along the longitudinal axis of instrument 30. This reduction of the effective length of shaft 52 causes the supporting portion of shaft 52 to withdraw into insertion portion 42. The medical personnel performing the insertion procedure can maintain a grasp on handle portion 41 while squeezing branch portions 49 with his/her fingertips positioned on finger pads 53. For example, the medical personnel's thumb can rest on one finger pad 53 and the medical personnel's forefinger can rest on the other finger pad 53 The shape and concavity of finger pads 53 serves to naturally position the fingers properly over the trigger portion. This permits instrument 30 to be held stationary while punctum plug 60 is released smoothly and accurately.

Figure 10:
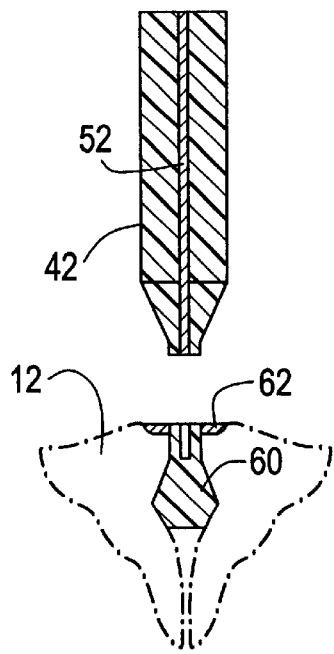
FIG. 10 is a sectional view of the instrument of FIG. 1 taken along line 8—8 of FIG. 7 with the insertion portion separated from the punctum plug.

As illustrated in FIG. 9, during withdrawal of shaft 50, insertion portion 42 of body 40 can be held in abutment with punctum plug 60, so that punctum plug 60 is prevented from being unseated. After release of punctum plug 60, instrument 30 can be removed as illustrated in FIG. 10. Instrument 30 can be disposed of or sterilized for reuse.

The invention can be easily manufactured through conventional insert molding methods. In particular, body 40 can be molded of a single material, such as medical grade polycarbonate, medical grade nylon or any other inert, latex free material that can withstand gamma irradiation for sterilization, with shaft 50 insert molded therein. Projections 47 can be "kiss-molded" around portions of shaft 52 or can merely oppose the surface of shaft 52. Further, projections 47 can be elongated in a direction orthogonal to shaft 52 to insure reliable contact with shaft 52. Body 40 can be made integrally as one piece with shaft 50 being the only additional part of instrument 30. Alternatively, insertion portion 42 can be defined by a separate tube, made of medical grade stainless steel or the like, insertion molded in body 40. Therefore, instrument 30 can be manufactured easily and inexpensively. Also, the integral and flexible nature of body 40 provides good tactile feedback during a punctum plug insertion process. Aggressive EDM knurling, diamond knurling, or other rough surfaces can be formed on handle portion 41 and/or flexible portion 46 to facilitate handling and manipulation. Passages 43 (see FIG. 1) can be formed through handle portion 41 to reduce the weight of instrument 30 and improve tactile feedback without reducing the rigidity of handle portion 41 excessively.

Figure 11:
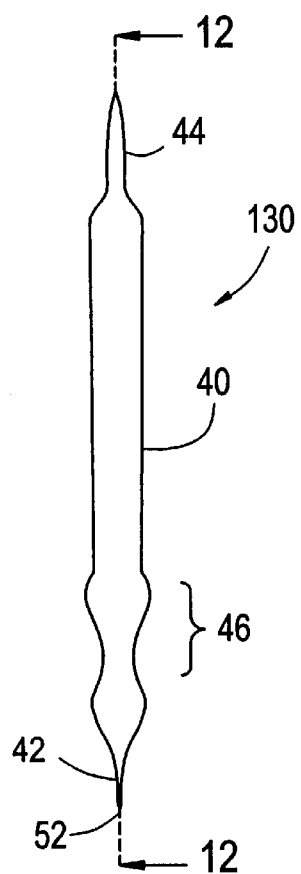
FIG. 11 is a side view of an insertion instrument in accordance with a second preferred embodiment.
Figure 12:
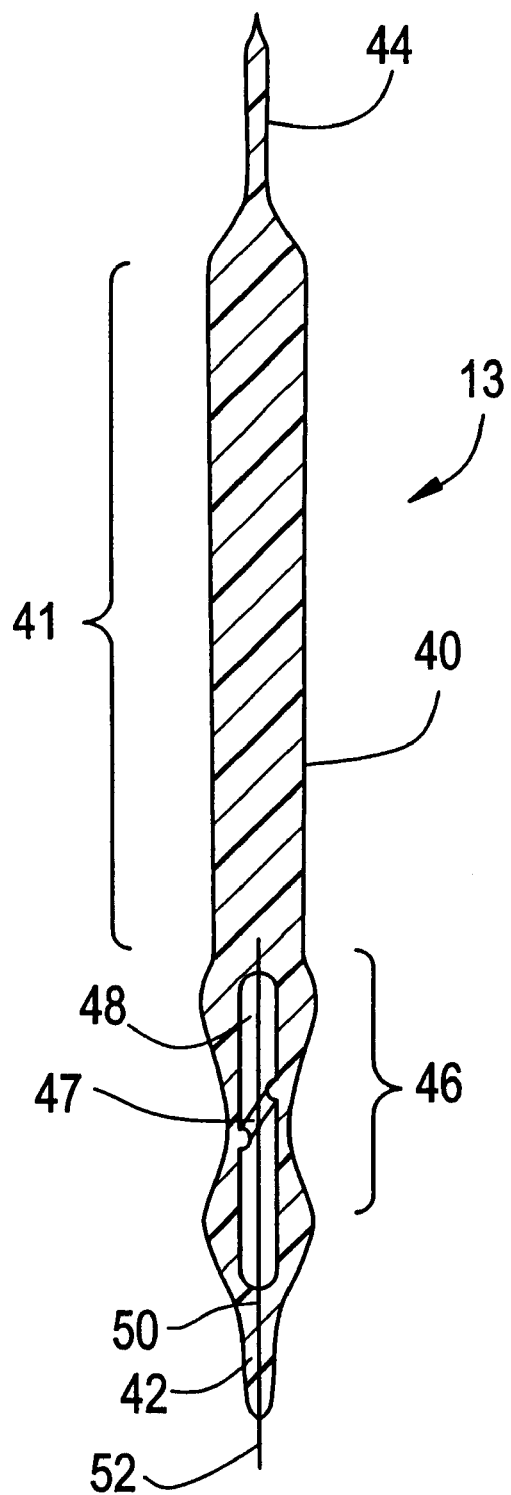
FIG. 12 is a sectional view of the instrument of FIG. 9 taken along line 12—12 of FIG; 11

FIGS. 11 and 12 illustrate a second preferred embodiment of the invention in which it can be seen that instrument 130 has body 40 that is generally cylindrical. Cavity 48 is formed in body 40 at a position adjacent plug insertion portion 42 to define flexible portion 46 as a hollow portion of body 40 having relatively thin walls. Accordingly, flexible portion 46 is more flexible than handle portion 41 of body 40. As illustrated in FIG. 10, projection 47' is formed on an inner surface of the thin walls of flexible portion 46. In particular, projection 47 comprises a helical elongated bump extending along the thin walls of flexible portion 46. Other aspects of the second preferred embodiment are similar to the first preferred embodiment and similar elements are labeled with like reference numerals.

The insertion procedure using the second preferred embodiment is similar to that using the first preferred embodiment. However, pressing any two opposed sides of flexible portion 46 will cause deformation of flexible portion 46 thereby causing projection 47 to bend shaft 52, and reduce the effective length of shaft 52 to withdraw shaft 52 into insertion portion 42 and release a punctum plug as described above with reference to the first preferred embodiment. An opening can be defined in flexible portion 46 to facilitate molding of instrument 130. Body 40 can be molded of two pieces that are subsequently joined using an adhesive or welding procedure.

Figure 13:
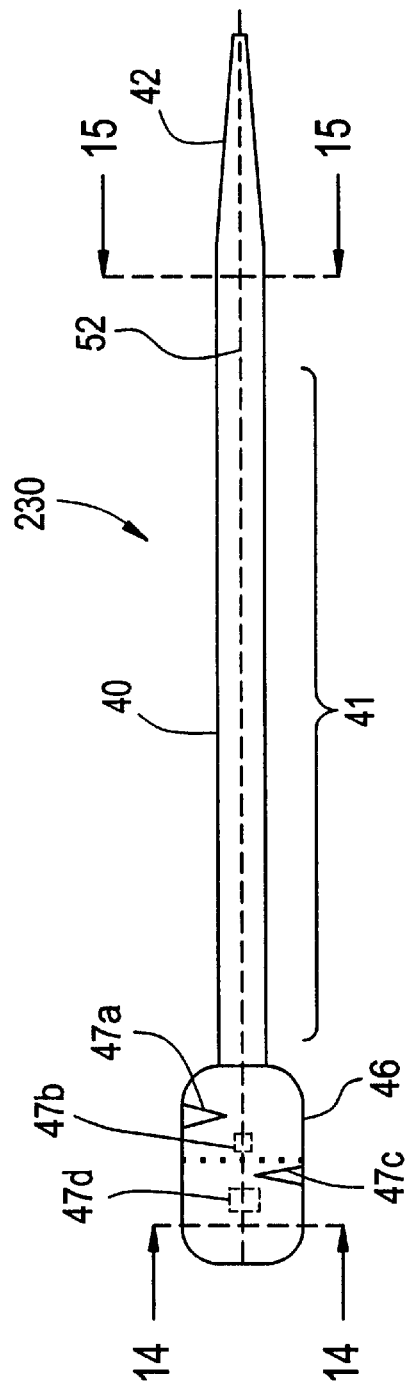
FIG. 13 is a side view of an inserting instrument in accordance with a third preferred embodiment of the invention.
Figure 15:
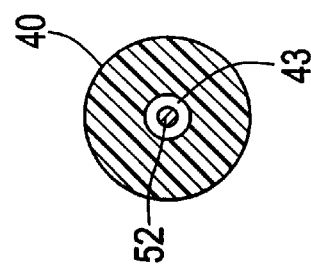
FIG. 15. is an enlarged sectional view taken along line 15—15 of FIG. 13.
Figure 14:
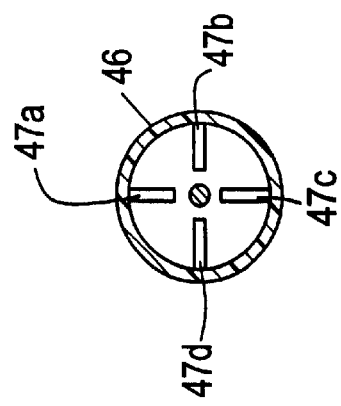
FIG. 14 is a sectional view of the instrument of FIG. 11 taken along line 14—14 of FIG. 13.

FIGS. 13–15 illustrate a third preferred embodiment of the invention. Instrument 230 includes body 40 comprising insertion portion 42, handle portion 41, and flexible portion 46 in the form of a bulb on a proximal end of instrument 230. Shaft 52, in the form of a wire, is fixed to a proximal end of the bulb, by being in-molded for example. Shaft 52 extends through the bulb and canulated portion 43 formed in handle portion 41 and insertion portion 42 (see FIG. 13). An end of shaft 52 normally extends from insertion portion 41 to define a plug support portion. As best illustrated in FIG. 12, the bulb a thin-walled portion having projections 47a, 47b, 47c and 47d formed in an inner surface thereof. Squeezing the bulb will push opposing pairs of projections 47a–d towards shaft 52 to bend shaft 52 and decrease the effective length thereof thereby releasing a plug from the supporting portion in a manner similar to the first and second preferred embodiments described above. Projections 47a–d of the third preferred embodiment are not molded around shaft 52. However, projections 47a–d could be molded around shaft 52 in a manner similar to the first preferred embodiment described above. Also, projections 47a–d could be replaced with a helical bump. The bulb can be molded in the same molding step as the rest of body 40 or can be molded separately and attached through use of an adhesive, welding, or the like. The bulb can be formed in two or more pieces that are attached as indicated by the dotted line in FIG. 11. The bulb can be formed of medical grade polypropylene or any other appropriate elastomer. The bulb can have openings to facilitate manufacture and operation thereof.

The flexible portion can be defined in any manner and can be located anywhere on the instrument, and there can be any number of projections associated therewith. For example, the flexible portion can be defined by three or more branch portions. One or more finger pads can be formed on any type of flexible portion. The cavity can be of any shape or size and can be enclosed or open to the exterior of the body. Any appropriate manufacturing methods can be employed to manufacture the instrument of the invention. The invention can be used to occlude the puncta, to place a stent in the puncta, to place a medical delivery device in the puncta, or to place any other prosthesis in the punctum. Accordingly, the term "plug", as used herein, refers to an occlusion device, a stent, a drug delivery device, or any other prosthesis to be inserted temporally or permanently in the puncta. Plugs can be placed in one or both of the upper punctum and the lower punctum. The body and or the plug can be color coded to indicate the type, size or other characteristics of the plug. The dilator can be formed of metal or another material and insert molded to other portions of the body cavity can be anywhere, projections need not be molded around wire either both punctum, color code, metal dilator.

The invention has been described through preferred embodiments. However, various modifications can be made without departing of from the scope of the invention as defined by the appended claims and legal equivalents.

What is claimed:

1. An instrument for inserting a plug into a lacrimal punctum said instrument comprising:
   an elongated body having a first end, a second end, a handle portion, a cavity formed in said body to define a flexible portion, and an insertion portion defined on said first end, said plug insertion portion having a passage formed therethrough in communication with the cavity formed in said body;
   a shaft coupled to said body and extending through the cavity formed in said body and the passage formed through said insertion portion, said shaft having a support portion defined thereon that is adapted to be received in an aperture formed in a plug; and
   a projection extending from an inner surface that defines the cavity in said body towards said shaft;
   wherein deformation of said flexible portion causes said projection to interact with said shaft to deform said shaft and reduce the effective length of said shaft thereby causing said support portion of said shaft to move from a position in which said support portion of said shaft extends from an end of the insertion portion to a position in which said support portion is substantially contained within said insertion portion.

2. An instrument as defined in claim 1, wherein said body comprises an integrally formed flexible material.

3. An instrument as recited in claim 2, wherein said flexible material is selected from the group consisting of a medical grade polycarbonate and a medical grade nylon.

4. An instrument as recited in claim 1, wherein said shaft comprises a wire having a first end fixed to said handle portion and a second end that has said support portion defined thereon.

5. An instrument as recited in claim 4, wherein said body is substantially cylindrical.

6. An instrument as recited in claim 4, wherein said flexible portion is disposed adjacent said insertion portion.

7. An instrument as recited in claim 4, wherein said flexible portion comprises plural branch portions having the cavity defined therebetween, each of said branch portions having a projection thereon.

8. An instrument as recited in claim 7, further comprising a finger pad defined on each of said branch portions.

9. An instrument as recited in claim 8, wherein each of said finger pads has a concave surface adapted to receive a user's fingertip to thereby position the user's fingers.

10. An instrument as recited in claim 4, wherein said flexible portion comprises a bulb.

11. An instrument as recited in claim 4, wherein said flexible portion comprises a hollow portion of said body having said cavity therein.

12. An instrument as recited in claim 4, further comprising a dilation portion defined on said second end of said body.

13. An instrument as recited in claim 12, further comprising gradations defined on said insertion portion.

14. An instrument as recited in claim 4, wherein a rough surface is defined on said body.

15. An instrument as recited in claim 4, further comprising a plug disposed on said support portion of said shaft.

16. An instrument as recited in claim 15, wherein said body is color coded to indicate characteristics of said plug.

17. A method of forming an instrument for inserting a plug into a lacrimal punctum, said method comprising the steps of:
   forming an elongated body having a first end, a second end, a handle portion, a flexible portion, a cavity defined in the flexible portion, and a plug insertion portion on the first end;
   forming a passage through the plug insertion portion and in communication with the cavity defined in the body;
   coupling a shaft to the body, the shaft extending through the cavity defined in the body and the passage formed through the insertion portion, the shaft having a support portion defined thereon that is adapted to be received in an aperture formed in the plug; and
   forming a projection extending from an inner surface of the body that defines the cavity in the body towards the shaft.

18. A method as recited in claim 17 wherein said steps of forming an elongated body, forming a passage, and forming a projection comprise molding the body as an integral unit.

19. A method as recited in claim 1, wherein said step of coupling the shaft to the body comprises insert molding the body around the shaft.

20. A method as recited in claim 1 wherein said step of forming an elongated body comprises insert molding the handle portion and the flexible portion around a tube defining the plug insertion portion.

* * * * *